(12) United States Patent
Tolton

(10) Patent No.: US 10,578,514 B2
(45) Date of Patent: Mar. 3, 2020

(54) REMOTE SENSING OF NATURAL GAS LEAKS

(71) Applicant: Synodon Inc., Edmonton (CA)

(72) Inventor: T. Boyd Tolton, Edmonton (CA)

(73) Assignee: New Era Technology, Inc., Boardman, OH (US)

( * ) Notice: Subject to any disclaimer, the term of this patent is extended or adjusted under 35 U.S.C. 154(b) by 172 days.

(21) Appl. No.: 15/630,882

(22) Filed: Jun. 22, 2017

(65) Prior Publication Data

US 2017/0370797 A1 Dec. 28, 2017

(30) Foreign Application Priority Data

Jun. 27, 2016 (CA) ..................... 2934093

(51) Int. Cl.
| | | |
|---|---|---|
| *G01M 3/38* | (2006.01) | |
| *G01N 21/3518* | (2014.01) | |
| *G01N 21/17* | (2006.01) | |
| *G01N 21/3504* | (2014.01) | |

(52) U.S. Cl.
CPC .......... *G01M 3/38* (2013.01); *G01N 21/3518* (2013.01); *G01N 2021/1793* (2013.01); *G01N 2021/3509* (2013.01); *G01N 2021/3531* (2013.01); *G01N 2201/0214* (2013.01); *G01N 2201/0216* (2013.01); *G01N 2201/068* (2013.01)

(58) Field of Classification Search
CPC ............................ G01M 3/38; G01N 21/3518
USPC ....................................................... 250/338.5
See application file for complete search history.

(56) References Cited

U.S. PATENT DOCUMENTS

| | | | | |
|---|---|---|---|---|
| 3,998,557 | A * | 12/1976 | Javan ..................... | G01N 21/39 356/434 |
| 2004/0232338 | A1 | 11/2004 | Tolton et al. | |
| 2010/0102232 | A1* | 4/2010 | Tolton .................... | G01J 3/457 250/339.07 |
| 2013/0289899 | A1* | 10/2013 | Tolton .................... | G01M 3/00 702/51 |
| 2015/0316415 | A1* | 11/2015 | Islam ..................... | G01J 3/453 250/338.4 |
| 2017/0176489 | A1* | 6/2017 | Choudhury ........... | G01N 29/02 |

(Continued)

OTHER PUBLICATIONS

European Office Action dated Feb. 25, 2019, in corresponding European Patent Application 17 177 688.3, filed Jun. 23, 2017 (7 pages).

(Continued)

*Primary Examiner* — David P Porta
*Assistant Examiner* — Abra S Fein
(74) *Attorney, Agent, or Firm* — Christensen O'Connor Johnson Kindness, PLLC

(57) ABSTRACT

A method of detecting natural gas releases that includes the step of traversing a target area with a gas-filter correlation radiometer having a field of view oriented towards the target area. The gas-filter correlation radiometer receives reflected radiation in a passband from the target area and produces gas-filter correlation radiometer signals from the received reflected radiation. A surface reflectivity spectral profile of the target area is determined. The presence of methane in the target area is then determined based upon the received reflected radiation and the surface reflectivity spectral profile of the target area.

6 Claims, 11 Drawing Sheets

(56) References Cited

U.S. PATENT DOCUMENTS

2018/0188163 A1* 7/2018 Kester .................. G01M 3/38

OTHER PUBLICATIONS

Mercier, J.A. et al., "SANDIA REPORT: Modeling, Sensor Design, and Performance Predictions for Gas Filter Correlation Radiometers," Sep. 1, 2012 (46 pages).

* cited by examiner

Fig. 3
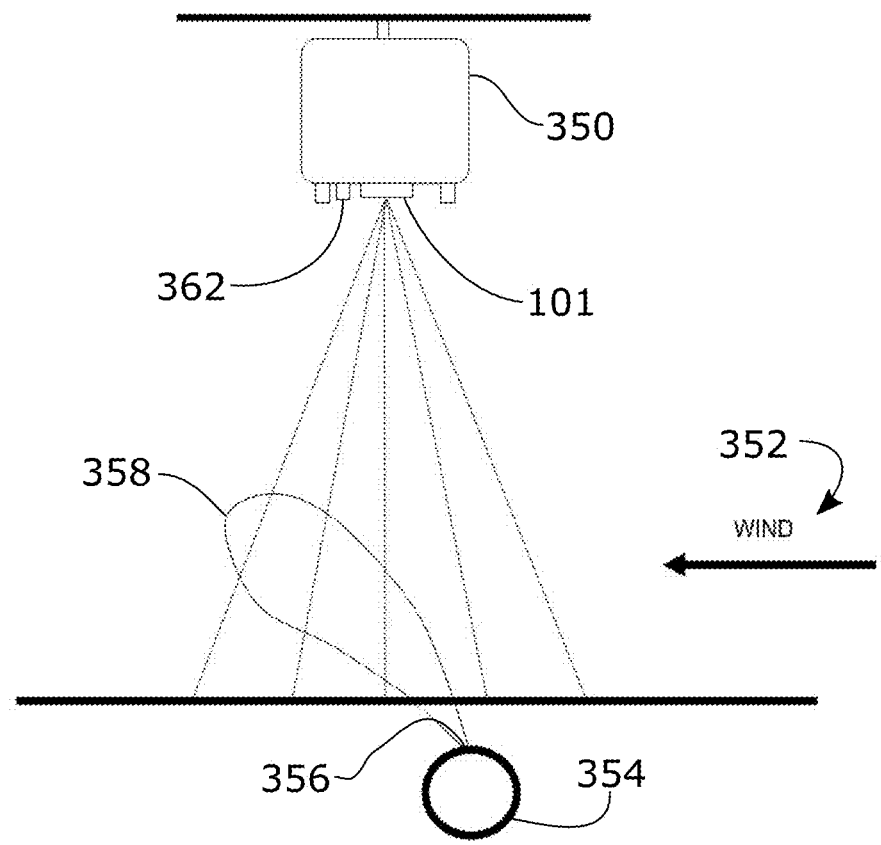
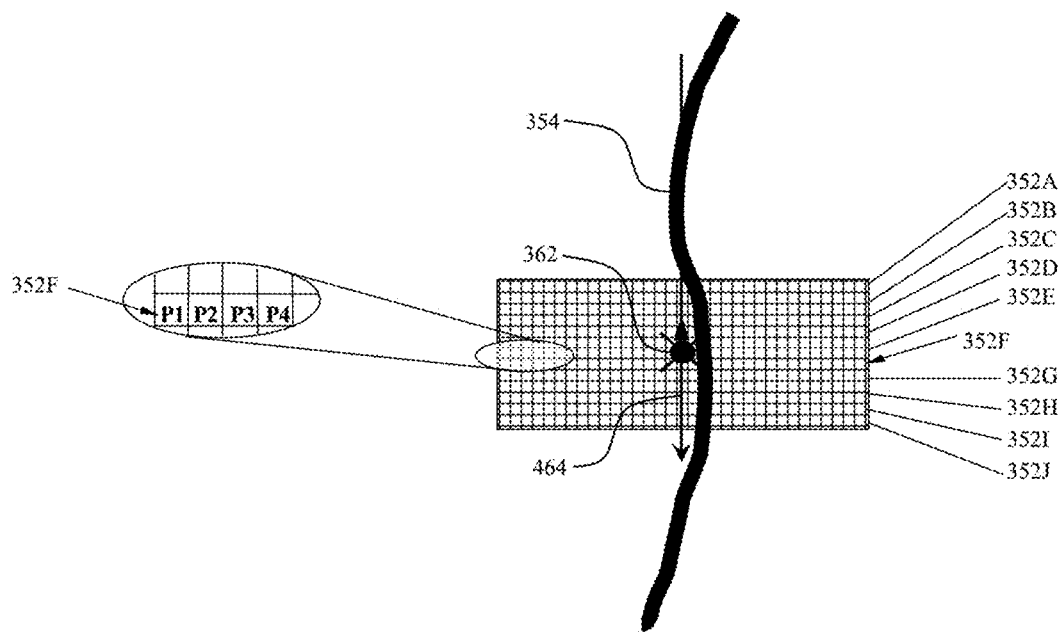
Fig. 4

REMOTE SENSING OF NATURAL GAS LEAKS

FIELD

Remote sensing of natural gas leaks.

BACKGROUND

This invention relates to remote sensing techniques to detect gas leaks. In particular, mounting a remote sensing instrument on a ground or aerial vehicle that can survey a target area, such as a pipeline, and measuring absorption of upwelling electromagnetic radiation that has passed through gas-filter correlation radiometer (GFCR).

A GFCR is a remote sensing radiometer that uses a sample of the gas as a spectral filter, providing enhanced sensitivity and selectivity to that gas. Incoming radiation is passed through a correlation cell, which is undergoing a gas-density modulation along its optical path. The radiation is then passed through a bandpass filter, which passes only a specific spectral (passband) range selected to cover an absorption band of the gas of interest. The radiation is then measured by an infrared detector. GFCRs have been used in different configurations for over three decades in remote sensing instrumentation.

Methane ($CH_4$) comprises approximately 95% of the composition of natural gas. However, $CH_4$ exists in fairly large quantities in the atmosphere (it is well mixed in the atmosphere with a concentration of approximately 1.7 ppm). Therefore, detecting a gas leak required detection of a small increase on a large background. Events such as passing near a source region of $CH_4$ (such as a farm) or an increase in the altitude of the airplane (an increase in the atmospheric path length) might result in the false signature of a leak.

To reduce the influence of the background, some past attempts have tried to detect the excess $CH_4$ of a natural gas leak by detecting the absorption of $CH_4$ in the infrared wavelength regions where the absorption bands are greatest for example, at 7.8 μm (2180 $cm^{-1}$) or 3.3 μm (3000 $cm^{-1}$). This provides the advantage that the upwelling radiation is primarily emitted from the earth's surface. This minimises the background $CH_4$, as only the $CH_4$ located between the remote sensing instrument and the earth's surface is detected. However, for underground pipe—since the temperature of the surface and the leaked $CH_4$ are nearly the same the radiative contrast between the surface and the leaked methane is very small, greatly reducing the detectivity/detectability of the leak. Also, the thermal noise introduced within the instrument itself becomes a serious design constraint.

As the background of $CH_4$ becomes very large, the solar radiation reaching the instrument would have passed through entire atmosphere. The best known satellite instrument to attempt to measure lower atmospheric trace gases using GFCRs was the MOPITT (Measurements Of Pollution In The Troposphere) instrument launched on NASA's Terra satellite. MOPITT was a satellite instrument launched in December 1999. MOPITT was designed to measure the concentrations $CH_4$ in the lower atmosphere utilising the 2.3 μm wavelength. The 2.3 μm $CH_4$ channels of MOPITT failed as the signal-to-noise ratio (SNR) of the measurements did not provide enough resolution to measure the concentration of $CH_4$ to a resolution ≤1%, which was required for global atmospheric chemistry models. As a consequence of this failure, attempts to measure $CH_4$ in lower atmosphere using the 2.3 μm wavelength have been discounted.

SUMMARY

In an embodiment, there is provided a gas filter correlation radiometer, comprising a bandpass filter, a beam splitter following the bandpass filter providing a first path through the gas filter correlation radiometer and a second path through the gas filter correlation radiometer; a gas correlation cell on the first path, the bandpass filter having a bandpass including at least part of the range of 4150 cm-1 to 4450 cm-1 and being arranged to filter radiation passing through the gas correlation cell, the gas correlation cell containing a gas having a spectral band within the bandpass of the bandpass filter overlapping a spectral band of the hydrocarbon; an evacuated cell on the second path; a first detector arranged to receive radiation that has passed along the first path and produce output comprising a first signal; a second detector arranged to receive radiation that has passed along the second path and produce a second signal; and detector electronics having the first signal and the second signal as input, the detector electronics being configured to compare the first signal and the second signal.

In an embodiment, there is provided a method of detecting a leak of a hydrocarbon, the method comprising traversing a target area with a gas filter correlation radiometer having a field of view oriented towards the target area, the gas filter correlation radiometer comprising a bandpass filter and a gas correlation cell, the bandpass filter having a bandpass including at least part of the range of 4150 cm-1 to 4450 cm-1 and being arranged to filter radiation passing through the gas correlation cell in a first path and through an evacuated cell in a second path, the gas correlation cell containing a gas having a spectral band within the bandpass of the bandpass filter overlapping a spectral band of the hydrocarbon; detecting radiation that has passed through the gas correlation cell to generate a first signal; detecting radiation that has passed through the evacuated cell to generate a second signal; and comparing the first signal and the second signal to determine if the hydrocarbon is present in the target area.

BRIEF DESCRIPTION OF THE DRAWINGS

There will now be described preferred embodiments of the invention, with reference to the drawings, by way of illustration only and not with the intention of limiting what is defined by the claims, in which like numerals denote like elements and in which:

FIG. 3 depicts a helicopter using the gas filter correlation radiometer to detect a leak in a pipeline;

FIG. 4 depicts an overhead view of a helicopter traversing a pipeline and shows successive fields of view, including an exploded view of a portion of a field of view being sampled;

DETAILED DESCRIPTION

In this document, the word "comprising" is used in its non-limiting sense to mean that items following the word in the sentence are included and that items not specifically mentioned are not excluded. The use of the indefinite article "a" in the claims before an element means that one of the elements is specified, but does not specifically exclude others of the elements being present, unless the context clearly requires that there be one and only one of the elements.

Leaks may be detected using a short wavelength absorption band of $CH_4$—for example, at 2.3 μm (4350 $cm^{-1}$)—to measure $CH_4$ leaks, and detecting this short wavelength absorption band may have a number of benefits over measurements at longer wavelengths—for example, at 3.3 μm or 7.8 μm. For example, the absorption lines of $CH_4$ at 2.3 μm are denser, the amount of solar energy is significantly higher, the reflectivities of most surface types are higher, and the upwelling thermal energy emitted by the surface is significantly less.

The instrument used for detection of leaks is a type of gas-filter correlation radiometer (GFCR). GFCRs have been used in different configurations for over 3 decades in remote sensing instrumentation.

The following terminology is used concerning signals in the realSens™ detector instrument: the COR signal is a signal measuring the light passing through a correlation cell (containing a gas, such as $C_2H_6$ or $CH_4$), the REF signal is a signal measuring the light that passed through a reference cell not containing any optically active gas, the DIFF signal represents the difference between the COR and REF signals, the AVG signal represents the average of the COR and REF signals, and the D2A signal represents the ratio of the DIFF and AVG signals.

Figure 1:
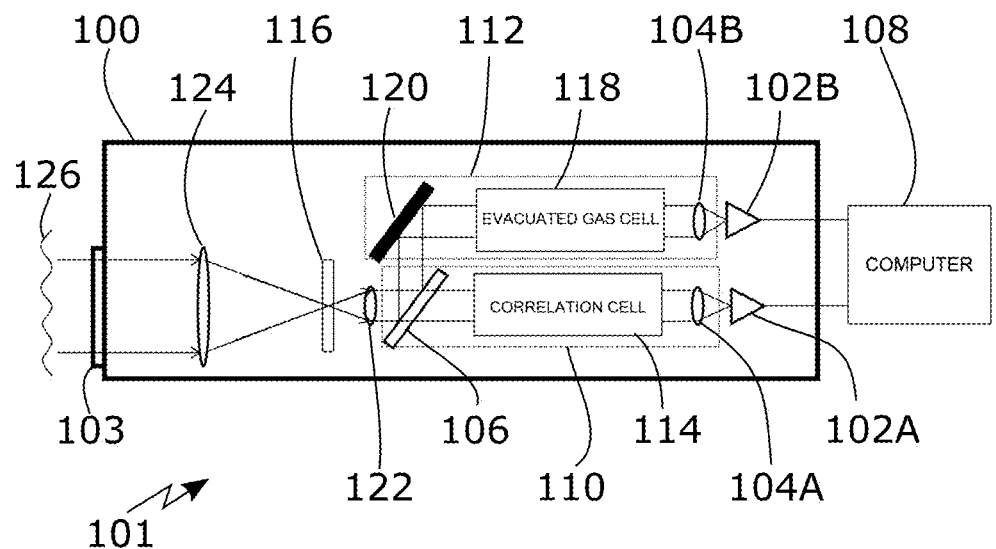
FIG. 1 is a schematic of the gas filter correlation radiometer.
Figure 2:
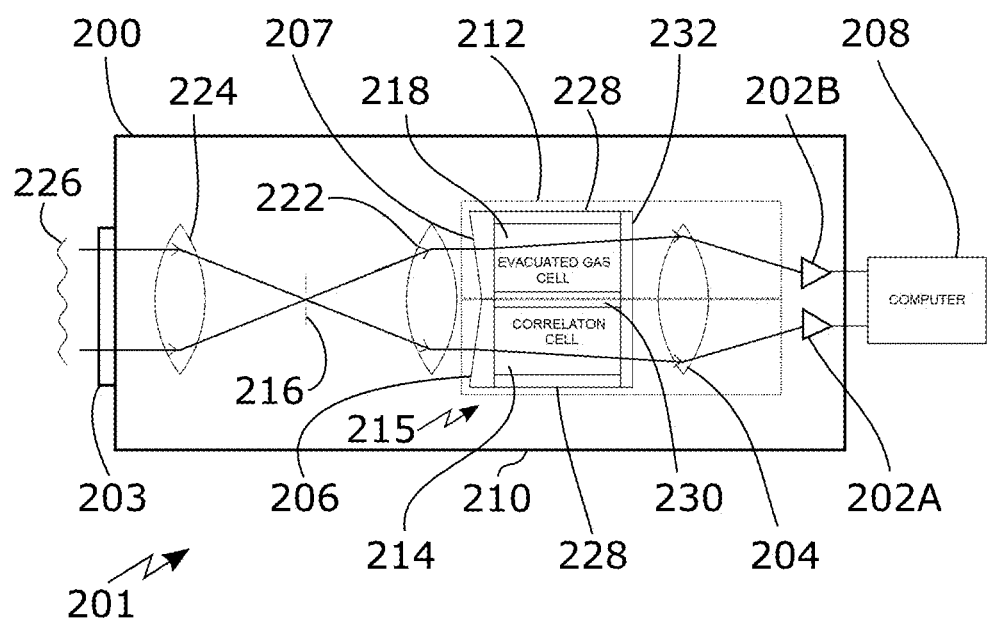
FIG. 2 is a schematic of an alternative embodiment of the gas filter correlation radiometer.
Figure 23:
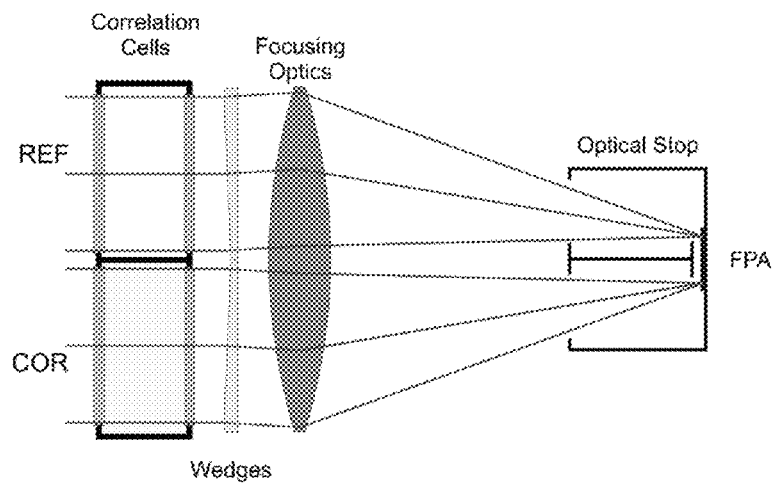
FIG. 23 is a schematic of the optical configuration of realSens™ radiometer.
Figure 24:
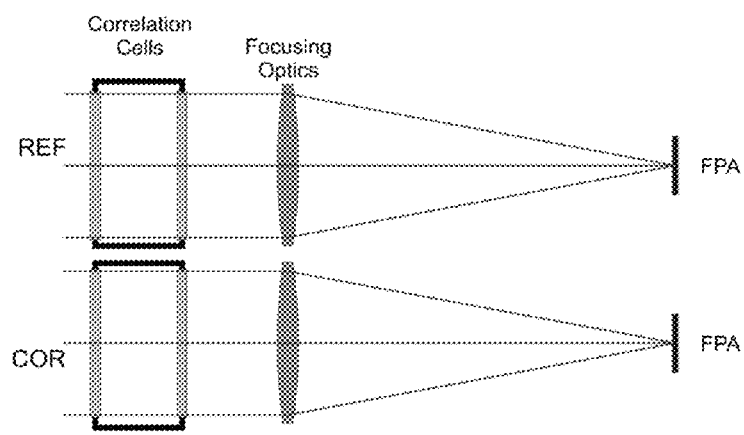
FIG. 24 is a shematic of an alternative embodiment of the optical configuration of realSens™ radiometer using a two focal plane array (FPA) configuration.

The basic concept of the instrument is a standard GFCR configuration, consisting of two radiometers viewing the same FOV (field of view). For example, this may be achieved using a single optical chain by splitting the optical chain in the middle and using wedges to separate the focused image of each side onto a single Focal Plane Array (FPA). FIG. 23 shows a schematic of this configuration. In a realSens™ detector, the FPA may consist of two 32×1 linear array separated by 10 mm. An alternate configuration which could be considered is to completely separate the REF and COR channels into two separate optical chains, as shown in FIG. 24. This may make the optical design easier but would require two separate detector systems (FPAs) and alignment of the FOVs would be more difficult to ensure. FIGS. 1 and 2 show in more detail possible configurations of a realSens™ detector instrument and FIGS. 3 and 4 show exemplary use of these configurations.

Referring to FIG. 1, there is shown a GFCR 101 incorporated within a housing 100, with a detector section, such as a pair of photodiode arrays 102A, 102B mounted in the housing. Radiation from source 126 passes through a window 103 in the housing 100 is collected by collector optic 124 and filtered by bandpass filter 116 and then directed by collimating lens 122 onto beam splitter 106. The bandpass filter 116 has a bandpass including at least part of the range of 4150 cm-1 to 4450 cm-1 and is arranged to filter light passing through the gas correlation cell, the gas correlation cell containing a gas having a spectral band within the bandpass of the bandpass filter overlapping a spectral band of the hydrocarbon. The gas may for example be methane or ethane. The bandpass may include at least part of the range 4175 cm-1 to 4275 cm-1 or a range of the range of 4150 cm-1 to 4450 cm-1. In an exemplary embodiment, a 40 $cm^{-1}$ wide band-pass filter 116 centred at 4350 $cm^{-1}$ is specified. The filter width is 1.3% of the central wavenumber. The passband of filter 116 may be selected to include an ethane or methane absorption peak and exclude radiation falling outside of the peak. Beam splitter 106 formed by a partially reflective mirror splits the radiation from the radiation source 126 along paths 110 and 112. On the first radiation path 110, the radiation passes through gas correlation cell 114 and is focused by detector lens 104A onto a detector, here a photodiode 102A. On the second radiation path 112, the radiation is directed by mirror 120 through an evacuated gas cell 118 and is focused by lens 104B onto a second detector, here photodiode 102B. The gas correlation cell 114, also called a gas filter or absorption cell, contains a gas, such as methane or ethane, to be detected.

The gas correlation cell 114 may for example be a 1 cm cell with for example a concentration of ethane provided by one atmosphere of pure $C_2H_6$. The second path 112 has a different path length of $C_2H_6$, such as may be obtained by providing the cell 118 with for example no $C_2H_6$, as for example an evacuated gas cell or a cell containing a gas that is optically neutral in relation to the ethane spectra of interest. The output of the photodiodes 102A, 102B is provided to suitable electronics, such as a computer 108, for processing according to gas filter correlation radiometer techniques. The GFCR 101 may use a beam splitter, for example, in the form of a partially reflective mirror as shown in FIG. 1, or in the form of a bi-prism, as shown in FIG. 2, or may selectively direct the incoming radiation through separate paths, in a time division manner, using for example a chopper. The use of a beam splitter versus a chopper is a trade-off between simultaneity of the two received signals and loss of signal intensity. A beam splitter, such as a partially reflective mirror or a bi-prism, is preferred for gas leak detection because it provides simultaneous measurement of both detector signals. This can be important because the signals are fast varying due to the forward motion of the helicopter and the variation in the reflective surface.

A different optical configuration is shown in an alternative embodiment in FIG. 2. Radiation from source 226 passes through a window 203 in housing 200, is collected on collector optic 224 and focused to a field stop 216. The field stop 216 is used to limit the field of view. The radiation from source 226 is then directed by collimating lens 222 onto prisms 206 and 207 which form the front of a compound gas cell 215 formed by gas cell walls 228, gas cell separator 230, and a plane parallel gas cell window 232. The prisms 206 and 207 split the radiation from the radiation source 226 along paths 210 and 212 by causing the radiation to diverge while passing through gas cells 214 and 218. On the first radiation path 210, the radiation is directed by prism 206 through gas correlation cell 214 and is focused by detector lens 204 onto the photodiode 202A. On the second radiation path 212, the radiation is directed by the prism 207 through an evacuated gas cell 218 and is focused by detector lens 204 onto photodiode 202B.

The compound gas cell 215 with prisms 206 and 207 may also be located between the field stop 216 and the collimating lens 222, or between the detector lens 204 and the photodiodes 202A and 202B. Likewise, the prisms 206 and 207 may be located at either the front of the compound gas cell 215 or at the back of the compound gas cell 215.

The gas correlation cell 214, also called a gas filter or absorption cell, contains a gas, such as ethane, to be detected. The gas correlation cell 214 may for example be a 1 cm cell with for example a concentration of ethane provided by one atmosphere of pure $C_2H_6$. The second path 212 has a different path length of $C_2H_6$, such as may be obtained by providing the cell 218 with for example no $C_2H_6$, as for example an evacuated gas cell or a cell containing a gas that is optically neutral in relation to the ethane spectra of interest. The output of the photodiodes 202A, 202B is provided to suitable electronics, such as computer 208, for processing.

The detector signal on the path 112 is:

$$S_1 = G \int_{\lambda_1}^{\lambda_2} I_\lambda \tau_{filter} d\lambda$$

where $I_\lambda$ is the intensity of the radiation from the radiation source 126, $\tau_{filter}$ is the transmissivity of the filter 116, $\lambda_1$ is the low pass of the filter 116, $\lambda_2$ is the high pass of the filter 116 and G is the gain of the photodiode 102B.

The detector signal on the path 110 is:

$$S_2 = G \int_{\lambda_1}^{\lambda_2} I_\lambda \tau_{filter} \tau_{corr.cell} \, d\lambda$$

where $\tau_{corr\ cell}$ is the transmissivity of the correlation cell 114.

If $$S_{avg} = \frac{S_1 + S_2}{2} \text{ and } S_{diff} = S_1 - S_2,$$

then the calculation made by the computer is:

$$S_{inst} = \frac{S_{diff}}{S_{avg}},$$

which yields a signal that is dependent on the presence of the target gas in the radiation path from the source 126 to the photodetector 102B. The calculation of the difference in the received signals for both optical paths is made for each pixel of the photodetectors 102A, 102B to yield an image of the field of view that may be displayed on a monitor.

FIG. 3 shows a manner of use of the GFCR 101 shown in FIG. 1. Detecting a leak of a hydrocarbon requires traversing a target area with a gas filter correlation radiometer having a field of view oriented towards the target area. A helicopter 350 traverses a pipeline 354 with a GFCR 101 having a field of view 352 oriented towards the pipeline 354. The GFCR 101 is tuned to detect for example ethane by appropriate selection of the bandpass of the filter 116, and the gas filter 114 contains a sample of ethane. If a leak 356 exists in the pipeline 354, the presence of ethane in the resulting plume 358 that may be moved by the presence of wind 360 will be detected using the GFCR 101. There is a further step of identifying a leak upon the gas filter correlation radiometer detecting the hydrocarbon. The presence of a leak is indicated by for example displaying the received signal using a monitor that is provided as part of the computer 108. Pixels on the monitor display corresponding to detected ethane may be coloured to enhance the image. Other methods of indication of the presence of a leak may be used such as detecting a concentration of ethane in the path between helicopter 350 and the ground that exceeds a predetermined threshold, and providing an alarm. The threshold is determined readily by calibration of the radiometer and experimentation. Due to the remote sensing capabilities of the device, the GFCR does not have to fly through the plume in order to detect leaks. The GFCR measures the integrated column concentration of natural gas between the helicopter and the ground, regardless of where in this column the natural gas occurs.

In one embodiment as shown in FIG. 4, the field of view 352 covers an area of 128 $m^2$, representing a swath 64 m long by 2 m wide. The long but narrow swath of the field of view 352 leads to an overall view of the pipeline 354 or target area through the use of a technique known as pushbroom imaging. As the helicopter 350 advances along the helicopter path 464 over the pipeline 354 or other target area, successive swaths below the helicopter 350 and perpendicular to the helicopter path 464 are detected by the GFCR 101. At a first time interval, the detectors 102A and 102B would sample signals from the field of view 352A, followed moments later by 352B, followed again by 352C and so on.

In FIG. 4, the field of view 352F represents the current swath of the target area being detected by the detectors 102A and 102B. Detectors 102A and 102B have corresponding pixels having collocated fields of view 352F where each 2 m×2 m cell of the field of view 352F is sampled synchronously by detectors 102A and 102B. Therefore, the cell marked P1 would be detected by a first pixel representing a portion of the field of view collocated and synchronized on detectors 102A and 102B. The cell marked P2 would be detected by a second pixel collocated and synchronized on detectors 102A and 102B. The same can be said for the cells marked P3 and P4 and so on. All cells P1 to P32 along a line would be detected simultaneously.

Figure 22:
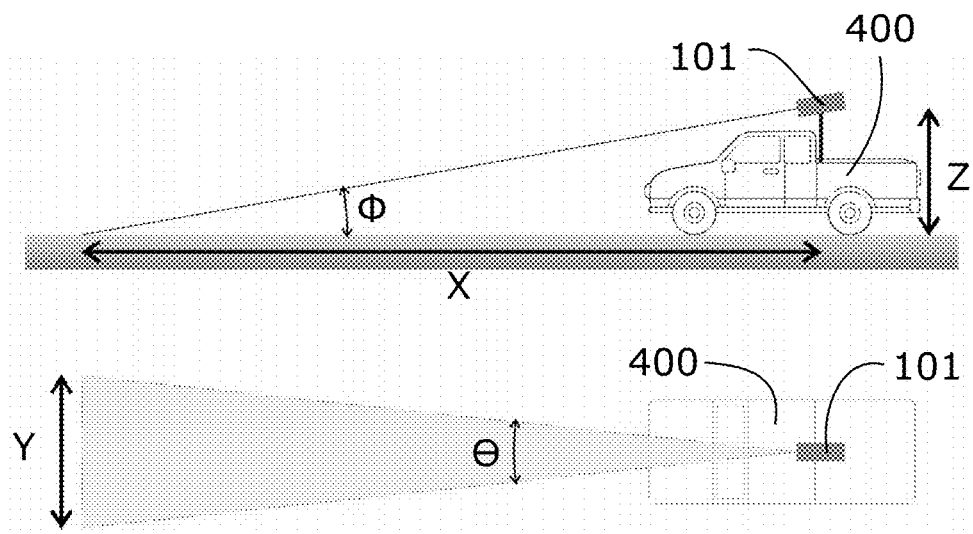
FIG. 22 is an illustration of the configuration of a truck-mounted embodiment of a 2.3 μm realSens™ radiometer.

In an exemplary embodiment, the GFCR 101 operates using ambient background radiation that passes through the plume 358 of natural gas. The upwelling radiation field is comprised of reflected solar radiation, radiation emitted from the surface, plus upwelling emission from the atmosphere. For operation during cloudy periods or at night, a source of illumination 362 may be used. For example, a powerful 1600 W Tungsten Halogen bulb may be mounted on the helicopter 350, with an IR transmitting window (not shown) and a focusing mirror (not shown). This mirror focuses the emission from the illumination source 362 to a 5 m spot on the ground. Assuming a lambertian reflective surface and a reflectivity of 5%, the reflected intensity at the surface would be 0.048 W m$^{-2}$. This is roughly equivalent to (or slight greater than) the reflected intensity of sunlight. The illumination source 362 should be mounted to reduce vibrations that could increase the signal to noise ratio of the detected signal. In an alternative embodiment, the GFCR 101 may be mounted on a different type of vehicle, such as a truck 400 as illustrated in FIG. 22, and driving the vehicle along a pipeline or other possible source of a gas leak. The GFCR 101 may also be tuned to detect other gases by selection of the bandpass of the filter 116.

The detected instrument signal is a function of the height of the natural gas column. For an atmospheric background concentration of 1 ppb of $C_2H_6$, the equivalent total atmospheric column thickness is approximately 8.5 μm. The equivalent $CH_4$ column thickness would be approximately 1700 times thicker.

A linear regression of the signal sensitivity between 0 and 4 mm of natural gas shows that the change in signal per mm of natural gas is $-1.69 \times 10^{-3}$ mm$^{-1}$. The measurement is actually detecting $C_2H_6$ which is assumed to be 2.5% of natural gas. Therefore, the detected columns of pure $C_2H_6$ are 40 times shorter than that of methane. Maximum sensitivity to $C_2H_6$ occurs at the lowest concentrations. This is the most desirable for detecting the smallest leaks.

Uncertainties may be introduced into the measurement by spectral interferences by other gases in the atmosphere (principally $H_2O$ and $CH_4$), variations in the surface emissivity, temperature variations in the atmospheric temperature, and variations in the altitude of the airplane. These uncertainties tend to reduce the sensitivity of the measurement to concentrations of natural gas, and variations may result in false signatures of leaks. The combined uncertainty is about +/−19 μm. This level of accuracy places a minimum limitation on the measurement's accuracy. Given a measurement resolution of $-1.69 \times 10^{-3}$ per mm natural gas, to measure a column height of ±19 μm a measurement precision of ±3.2×10$^{-5}$ (i.e., a signal-to-noise ratio of 31,000) is required. Such a measurement precision may be obtained from the GFCR 101, and may be adjusted by for example varying the length of the absorption cell 114.

The sensitivity of the instrument is ultimately a function of the amount of energy that is collected and focussed onto the detector element. This in turn is a function of the field-of-view (FOV) of the instrument (which determines the surface resolution), the size of the collector optic 124, the size of the detector pixel in the photodiodes 102A, 102B, the transmission of the instrument, and the observation period (frequency) of the instrument. The FOV and the collector optic size directly affect the energy collected, as the larger the optic and FOV, the more photons collected. However, they also directly affect the detector pixel size, due to the principle of etendue (AΩ) conservation in an optical chain. The transmission of the instrument directly affects the energy collected as any losses in the system directly reduces the number of photons incident on the detector. And finally, the pixel size and observation period directly affect the noise-equivalent power (NEP) of the detector.

Figure 25:
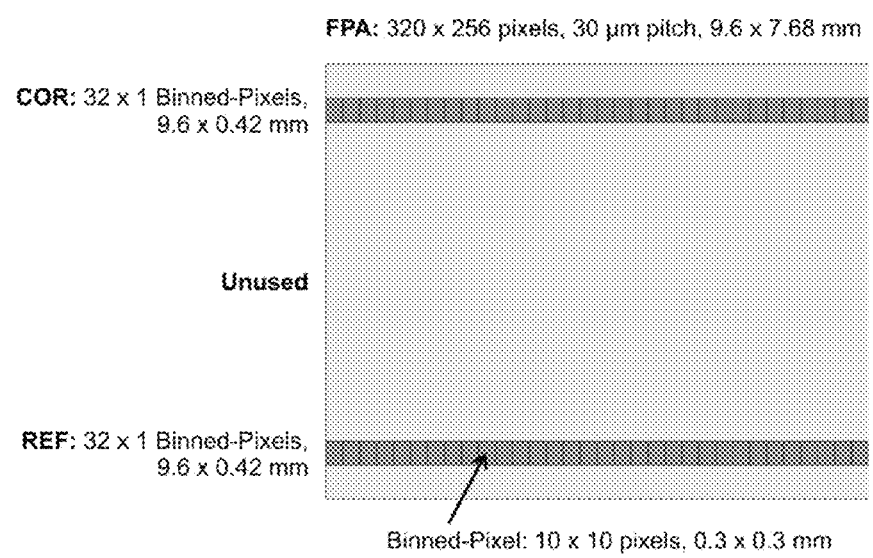
FIG. 25 is a schematic of a 320×256 pixel FPA with the proposed 32×1 binned-pixel arrays mapped.

Two versions of a 2.3 μm instrument based on the detector system are described below. In the first version the detector may be an off-the-shelf 320×256 Focal Plane Array (FPA) detector; in an example, the detector is a Xenics Xeva-2.5-320 extended InGaAs camera. The pixels may be "binned" so as to increase the signal-to-noise ratio and to produce the same (on-the-ground) Field of View (FOV) pixel size and shape as a realSens™ detector. The wider 320 pixel dimension may be the across track dimension. Thus to achieve a 32×1 sub-array of binned pixels with the same relative size as a realSens™ detector each "binned-pixel" may be 10×14 pixels in extent (140 pixels total). FIG. 25 shows a schematic of the FPA, showing a mapping of the proposed binned-pixels arrays. Given a desired on-the-ground FOV of 2×2.8 m realSens™ detector, this may result in a focal length for the 2.3 μm realSens™ detector of 45 mm.

The second version of 2.3 μm instrument may use a custom detector built as an FPA consisting of two 32×1 linear arrays with pixels of dimension 1×1.4 mm.

Figure 5:
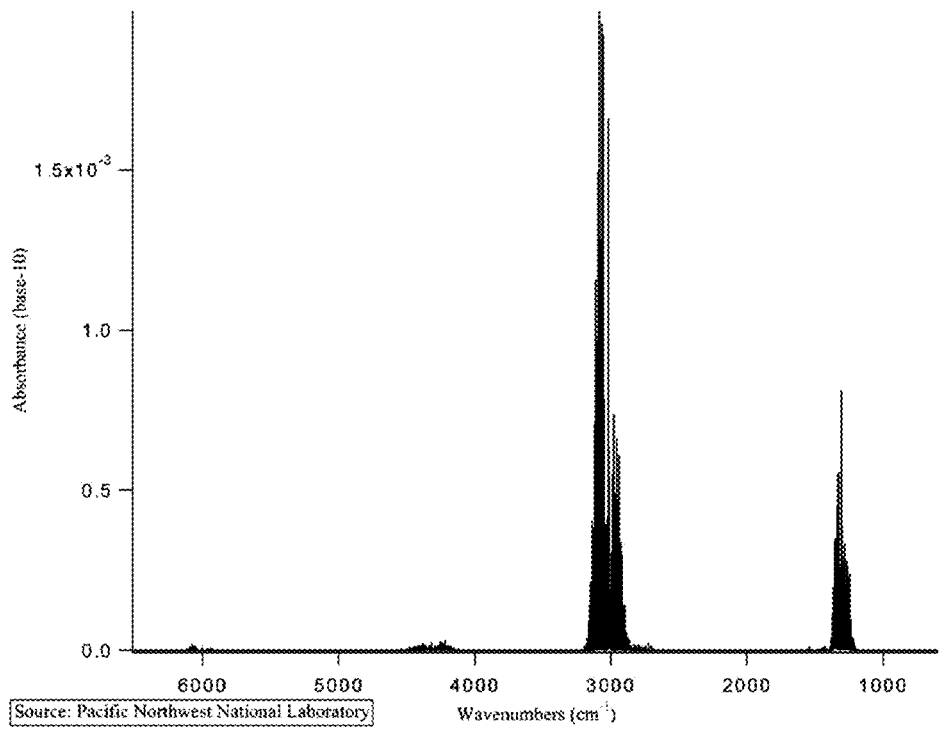
FIG. 5 is graph of the spectral absorbance of methane.
Figure 6:
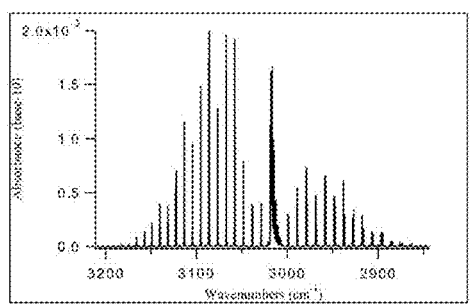
FIG. 6 is a graph of the spectral absorbance of methane in the 3.3 μm wavelength range.
Figure 7:
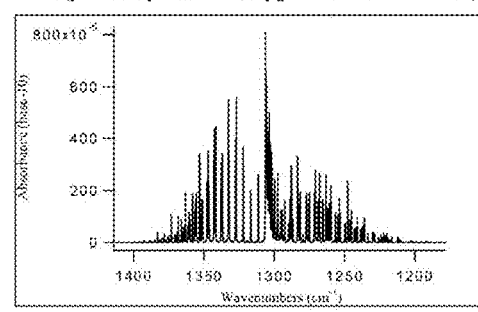
FIG. 7 is a graph of the spectral absorbance of methane in the 7.7 μm wavelength range.
Figure 8:
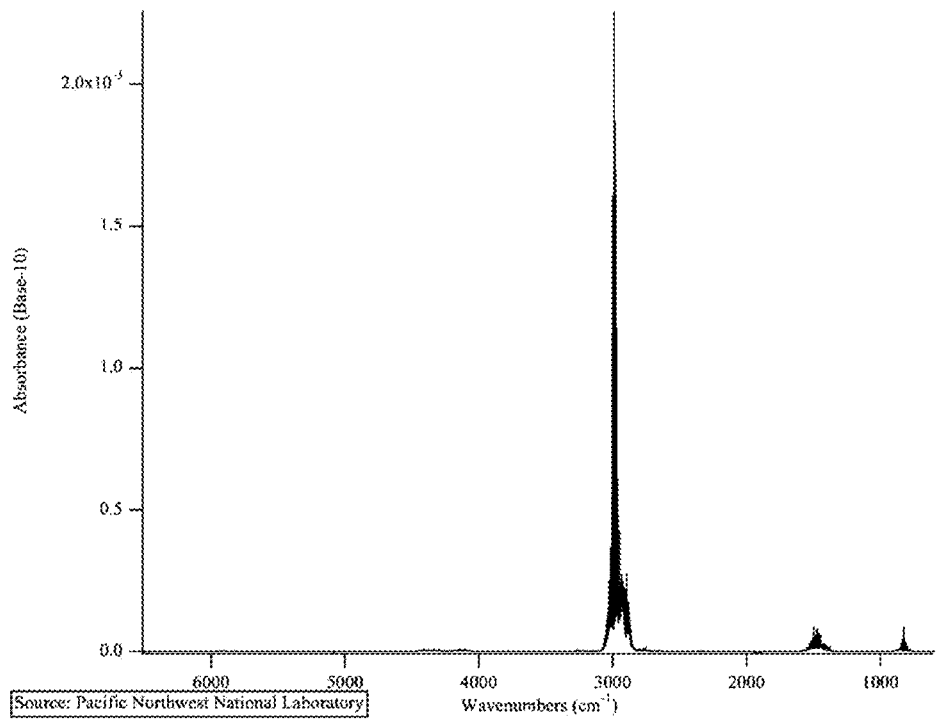
FIG. 8 is graph of the spectral absorbance of ethane.
Figure 9:
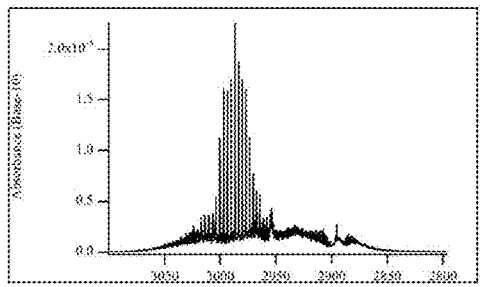
FIG. 9 is a graph of the spectral absorbance of ethane in the 3.3 μm wavelength range.
Figure 10:
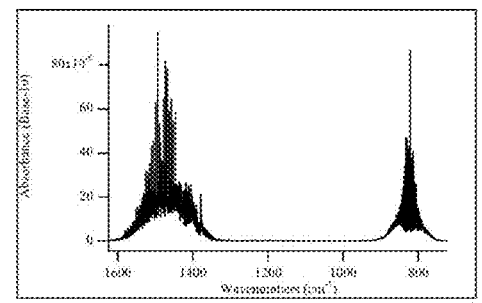
FIG. 10 is a graph of the spectral absorbance of ethane in the 6.7 μm and 12 μm wavelength ranges.

To detect leaks from hydrocarbon liquids pipelines, the detector system may be adapted using a method to make the detector system sensitive to a specific chemical by putting the vapour of the chemical into the correlation cell(s) of a gas filter correlation radiometer, which may be a realSens™ radiometer. The instrument was originally designed to measure ethane and methane in the 3.3 μm (3000 cm$^{-1}$) region. FIGS. 5-7 show the spectral absorption bands for methane from the Pacific Northwest National Laboratory (PNNL) database and FIGS. 8-10 and show the spectral absorption bands for ethane from the PNNL. This spectral region was originally chosen as it has the strongest spectral absorption features in the infrared, and therefore should theoretically provide the greatest sensitivity to methane and ethane.

However, although the spectral absorptions are very strong in the 3.3 μm region for methane and ethane, this is a spectral region with low radiances in the environment. Detected radiances are a combination of reflected solar radiation and terrestrially emitted radiance, both of which are low energy at these wavelengths. Also, the surface reflectivity for most surface types is quite low in this spectral region. These factors limit the sensitivity of the detection system using the 3.3 μm region, due to spatial variations in surface temperature and reflectivity. Also, since the environmental radiances are so low, the optics were designed to maximise the energy gathered (F/0.75, ≈12″ fore-optic, and 1.4×1.0 mm InSb pixels), and thus required a large and heavy instrument.

Instead, ethane and methane may be detected using the detection system at absorption bands in the 2.3 µm region (4350 cm$^1$). The 2.3 µm region has lower spectral absorption by the leaked gases than the larger wavelength absorption band, which initially suggests it would be unsuitable in the detection system. The 2.3 µm absorption bands of methane and ethane are approximately 50 times weaker than at 3.3 µm. However, the radiance at longer wavelengths is entirely terrestrial, which means a low spectral contrast between the background radiance and the leaked gas, if the leaked gas is of similar temperature as the background.

Methane Leak Sensitivity at 2.3 µm

Figure 11:
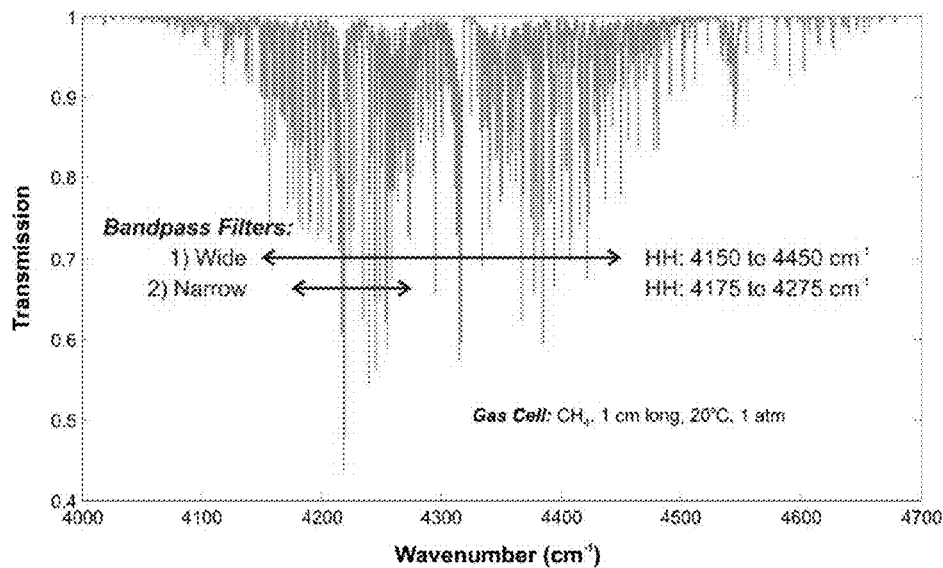
FIG. 11 is a graph of the transmission of a 1 cm long gas cell filled with 1 atm of $CH_4$ at 20° C. overlaid with a wide bandpass filter (4150 to 4450 $cm^{-1}$) and a narrow bandpass filter (4175 to 4275 $cm^{-1}$)
Figure 12:
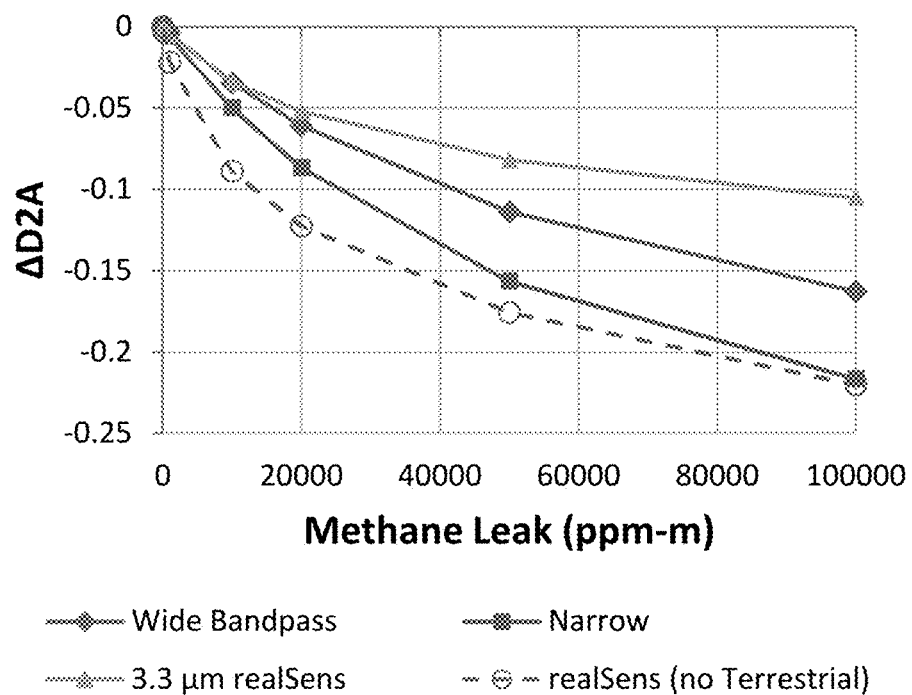
FIG. 12 is a graph of the sensitivity (ΔD2A) to leak methane for a wide bandpass filter, a narrow bandpass filter, a 3.3 μm realSens™ radiometer and a 3.3 μm realSens™ radiometer with no terrestrial emission included (a RealSens™ radiometer is a radiometer made by Synodon of Edmonton, Alberta, Canada, and is designed in accordance with the general description of the exemplary disclosed radiometer, other than use of the 2.3 μm peak and band.

FIG. 11 shows the 2.3 µm (4350 cm$^1$) transmission of a 1 cm long gas cell filled with 1 atm of $CH_4$ at 20° C. For the purpose of this analysis, two bandpass filters were considered, a wide filter covering most of the band (half heights: 4150 to 4450 cm$^1$, 300 cm$^{-1}$ wide), and a narrow filter covering a portion of the band with strong absorption (half heights: 4175 to 4275 cm$^1$, 100 cm$^{-1}$ wide). At these wavelengths, the terrestrial emission is negligible compared to the reflected solar radiance. FIG. 12 shows a GenARTS™ model calculation of the sensitivity of a 2.3 µm realSens™ to leaked methane, assuming a correlation cell of 10 cm and a pressure of 1 atm. The results shown in FIG. 12 show the change in D2A signal as a function of the leak concentration. It shows ≈33% higher sensitivity for the narrow bandpass, over the wide. Also included in the plot is the sensitivity of the 3.3 µm. Quite surprisingly, FIG. 12 shows lower sensitivity for the 3.3 µm realSens™. This may be caused by the following factors:

(1) The calculations for 3.3 µm realSens™ assumes the very wide bandpass filter profile, (2) The absorption lines of methane at 3.3 µm saturate quickly, and (3) The terrestrial emission at 3.3 µm significantly increases the AVG signal, lowering the D2A.

First, the 3.3 µm passband of realSens™ is very wide to maximise the energy gathering. This reduces the sensitivity, the same as shown with the 2.3 µm analysis. Second, although this figure seems to show similar sensitivities to methane, the rapid saturation of absorption lines in the 3.3 µm band quickly reduces the sensitivity at higher leaks (ppmm). Finally, the increase in the AVG signal due to terrestrial emissions greatly reduces the change in D2A due to leaks. To illustrate this effect, a fourth line was added to FIG. 12, showing the sensitivity of a 3.3 µm realSens if there was no terrestrial emission.

To further illustrate the sensitivities of 2.3 versus 3.3 µm realSens, Table 1 shows the sensitivity (ΔD2A per ppm-m $CH_4$) at low leak concentrations. This table shows: (1) the large reduction in sensitivity for the 3.3 µm realSens™ due to terrestrial emission and (2) the advantages of using a narrow bandpass filter.

TABLE 1

Sensitivity of realSens instruments to small leaks of methane.

| Instrument | Sensitivity (ΔD2A per ppm-m $CH_4$) |
| --- | --- |
| 2.3 µm realSens (wide) | −3.4 × 10$^6$ |
| 2.3 µm realSens (narrow) | −5 × 10$^6$ |
| 3.3 µm realSens | −3.4 × 10$^6$ |
| 3.3 µm realSens (no Terrestrial Emission) | −2.2 × 10$^5$ |

Sensitivity to Rsurf Variations

Figure 13:
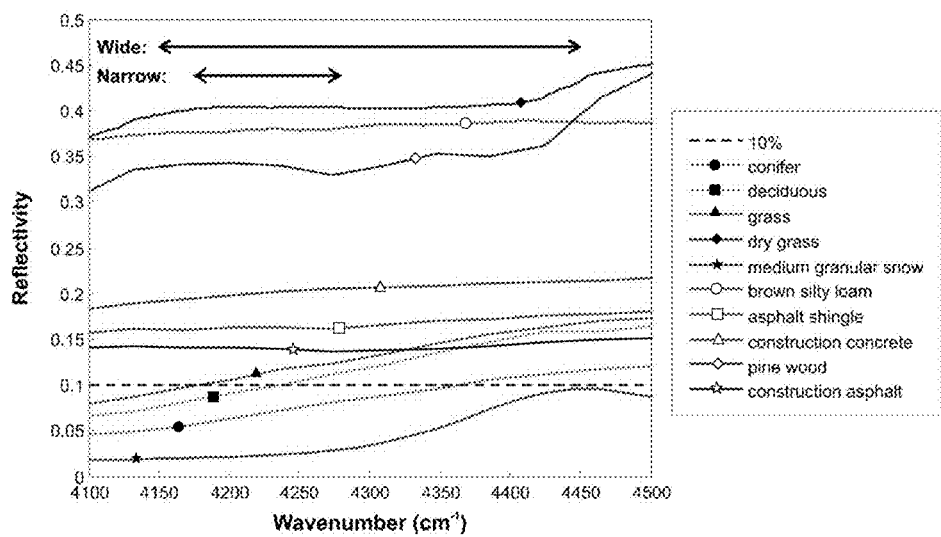
FIG. 13 is a graph of various surface types across the wide and narrow 2.3 μm bandpasses.
Figure 14:
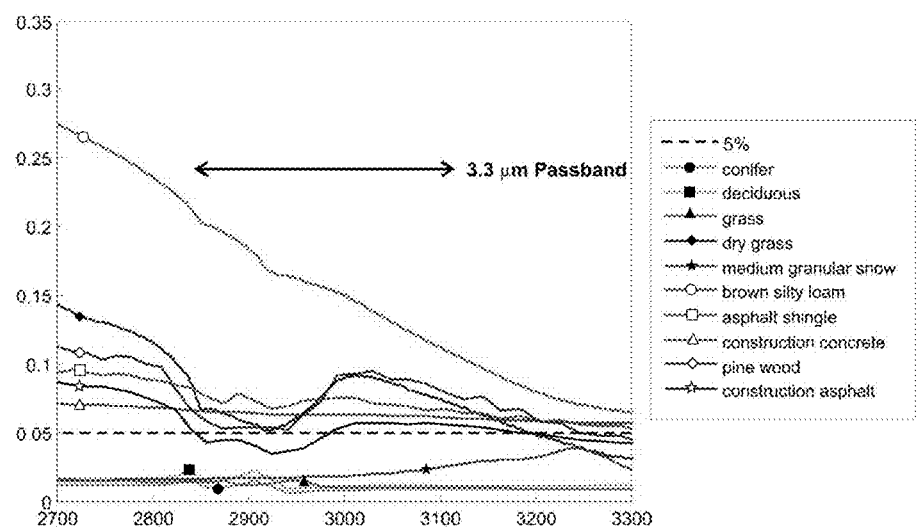
FIG. 14 is a graph of various surface types across the wide and narrow 3.3 μm realSens™ bandpass.
Figure 15:
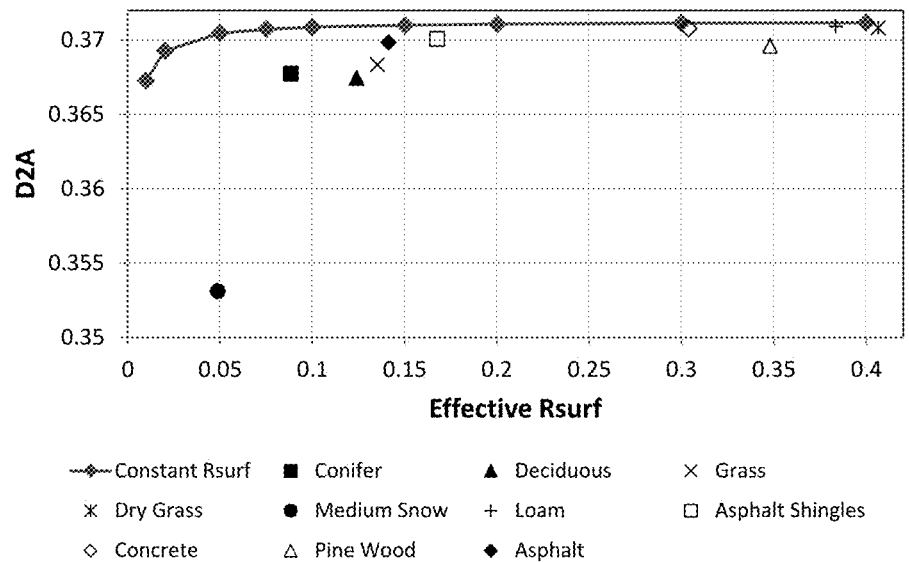
FIG. 15 is a graph of D2A signals as a function of effective Rsurf, for different surface types, for the wide bandpass 2.3 μm realSens™ radiometer.
Figure 16:
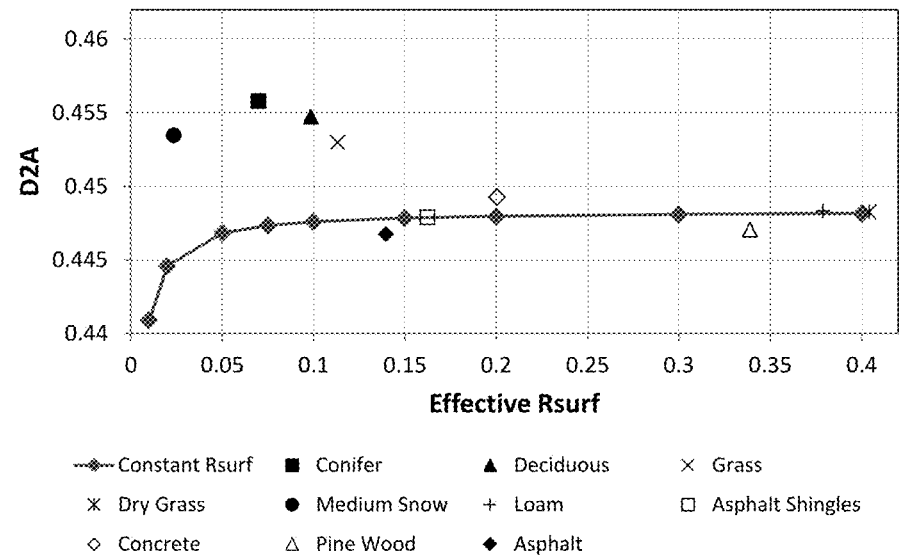
FIG. 16 is a graph of D2A signals as a function of effective Rsurf, for different surface types, for the narrow bandpass 2.3 μm realSens™ radiometer.
Figure 17:
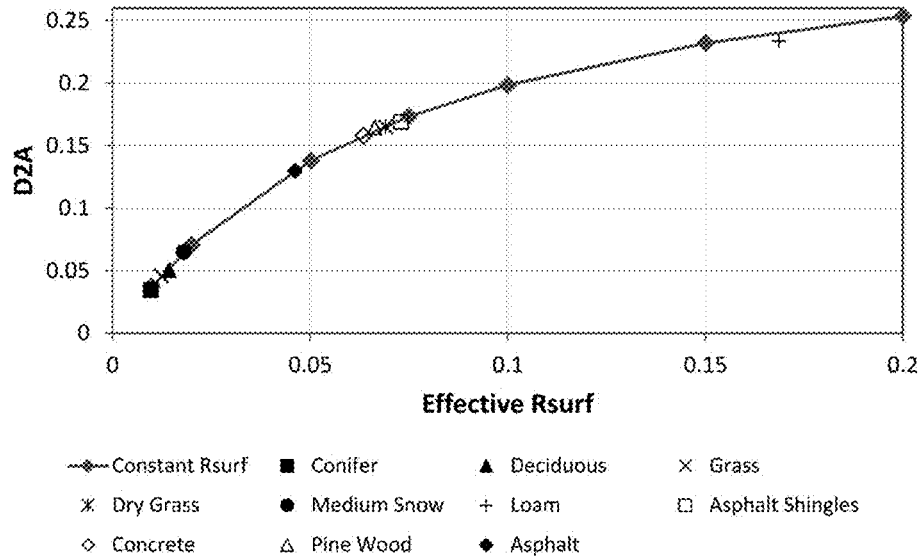
FIG. 17 is a graph of D2A signals as a function of effective Rsurf, for different surface types, for the 2.3 μm realSens™ radiometer.

One major impediment to maximising the sensitivity of a 3.3 µm realSens™ was the difficulty of accounting for variations in surface temperature, emissivity and reflectivity (Rsurf). An advantage of a 2.3 µm realSens™ radiometer is the fact that the terrestrial emission is very small compared to reflected solar radiances, removing the influence of varying surface temperature and emissivity. However, Rsurf variations across the passband are still significant. FIGS. 13-14 show the reflectivity of a number of "typical" surface types for the 2.3 and 3.3 µm bands. The 3.3 µm band shows significantly more structure in reflectivity than the 2.3 µm band. Also the 2.3 µm band shows higher reflectivities than the 3.3 µm band. FIGS. 15-17 shows the results for the modelled sensitivity to variations in Rsurf (uniform over passband) for a wide passband 2.3 µm realSens™, a narrow passband 2.3 µm realSens™, and the 3.3 µm realSens™, respectively. There are a number of observations to make comparing these figures.

The D2A signals for the narrow 2.3 µm realSens™ are higher than the wide 2.3 µm realSens. This is may be due to the narrower passband realSens™ having a higher absorption line density over the passband. The sensitivity to variations in uniform Rsurf is similar for the narrow and wide 2.3 µm realSens™. The largest variations occur at low Rsurf. The sensitivity to different surface types for the narrow and wide 2.3 µm realSens are similar.

The variations of D2A as a function of (uniform) Rsurf is very large. This is due to the fact that the model assumes surface emission varies with respect to Rsurf (Kirchoff's law: emissivity=1 reflectivity). As the Rsurf increases the emission from the surface decreases, making the signal detector "more solar" in origin. The model assumes the gas is the same temperature as the surface. Since the surface and the gas are the same temperature, the emission by the gas equals the absorption of the surface radiance by the gas. The result is no radiative contrast for the terrestrial component of the radiance.

This lack of radiative contrast is a very important consideration for the data retrieval for the 3.3 µm realSens™. Because the detected radiance is composed of reflected solar and terrestrially emitted radiance, the variation in D2A due to Rsurf variations (both uniform and within the passband) complicate data retrievals. Further complications come from the fact that (1) the Tsurf is also varying, (2) the leaked gas temperature is likely lower than Tsurf due to decompression, and (3) the relationship between Rsurf and surface emissivity used in the model (Kirchoff's law) does not actually hold. This is where the process of surface normalisation has been proposed to improve data retrievals for realSens.

For a 2.3 µm realSens™, the magnitude of terrestrial emission is negligible compared to reflected solar radiance. This removes a major source of complications which arose from 3.3 µm realSens™ analysis.

Calculation Parameters

Figure 18:
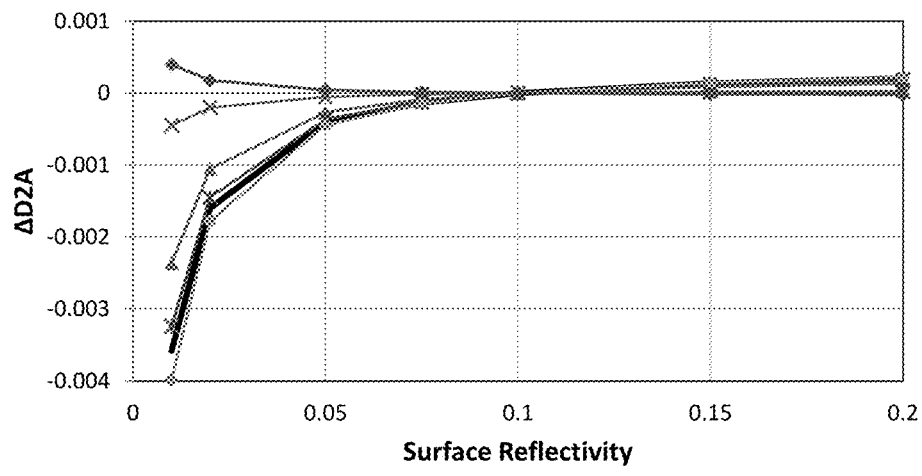
FIG. 18 is a graph of the change in D2A signal as a function of Rsurf, for modified calculation parameters using results from a wide bandpass 2.3 μm realSens™ radiometer
Figure 19:
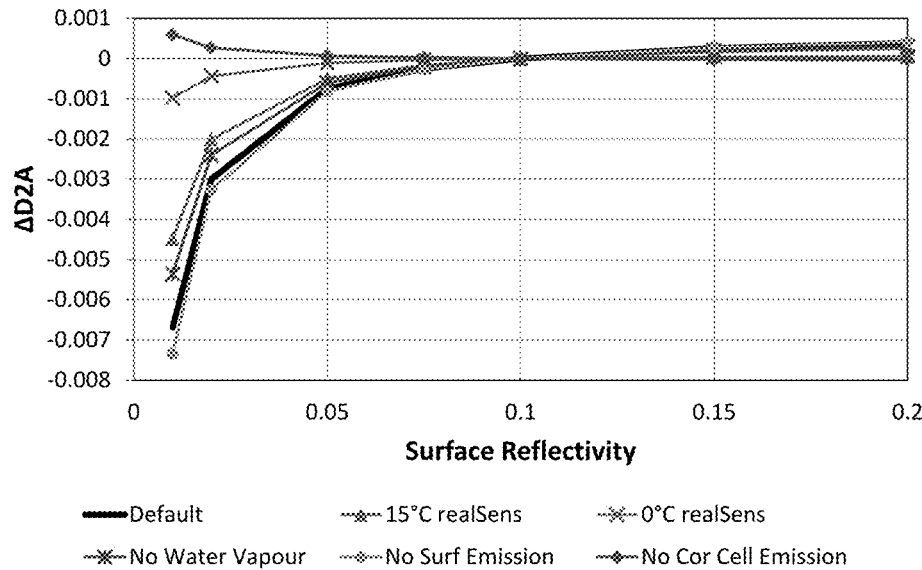
FIG. 19 is a graph of the change in D2A signal as a function of Rsurf, for modified calculation parameters using results from a 2.3 narrow bandpass μm realSens™ radiometer.
Figure 20:
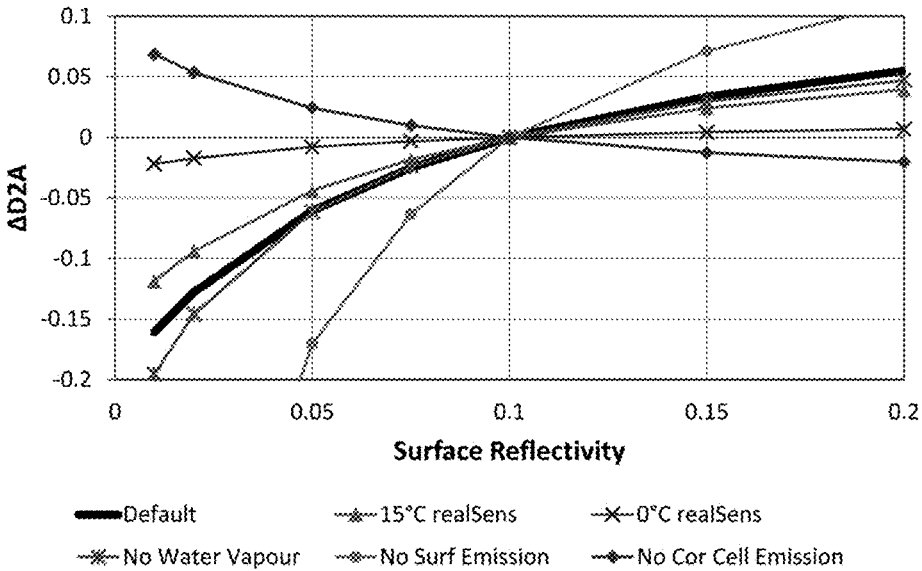
FIG. 20 is a graph of the change in D2A signal as a function of Rsurf, for modified calculation parameters using results from a 3.3 μm realSens™ radiometer.

The results presented above are dependent on many parameters about the environment and the instrument. To explore how variations in some of these parameters may add noise to measurements, models of changes to the values of a few important parameters were made. They include, (1) instrument temperature, (2) atmospheric water vapour, (3) surface emission, and (4) emission by the gas in the correlation cell of the detector instrument. FIGS. 18-20 shows the change in D2A signal as a function of Rsurf, for changes in the four instrument and environmental parameters, and for the 3 different instrument configurations (wide and narrow passband 2.3 µm realSens™ and the 3.3 µm realSens™). A number of observations can be made from these results:

(1) All instrument configurations show sensitivity to Rsurf, however the sensitivity of the 2.3 µm instrument configurations is significantly less than the 3.3 µm instrument. This may be due the detected emission at 2.3 µm being almost all reflected solar.
(2) The 2.3 µm instrument configurations do show some sensitivity to Rsurf variations. This may be due to the fact that although the terrestrial emission is extremely small, it still does make up a tiny component of the upwelling radiance.
(3) Reducing the gas temperature of the correlation cell significantly reduces the sensitivity of all configurations of the instrument to variations in Rsurf. However, in the extreme case of no radiative emission by the correlation cell gas (the equivalent of chopping the input radiance), the D2A sensitivity to Rsurf is minimal.
(4) The narrow passband version of the 2.3 µm instrument is more sensitivity to variations in model parameters than the wide passband. This may be due to the higher density of $CH_4$ absorption lines in the narrow passband.
(5) All instrument configurations show increased sensitivity to Rsurf if there is no emission from the surface. This is a small effect for the 2.3 µm configurations, but a massive effect for the 3.3 µm configuration (due to the different proportions of the upwelling radiance being composed of surface emission). This may be due to the gas in the atmosphere emitting at the wavelengths of the gas lines
(6) And finally, the effects of water vapour in atmosphere on the instrument are small.

2.3 µm Band of Ethane

Figure 21:
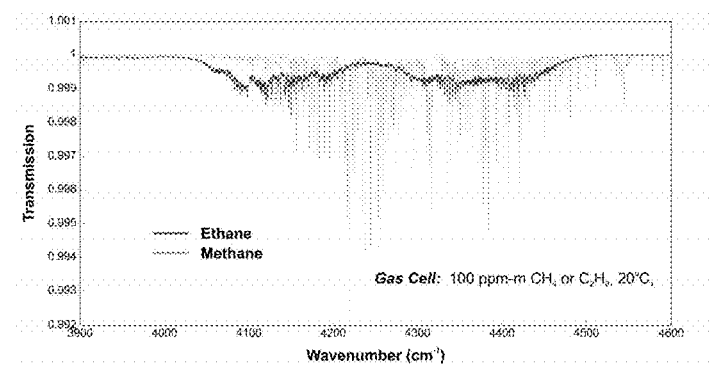
FIG. 21 is a graph of the transmission of a 100 ppm-m gas cell (at 20° C.) of ethane and methane.

Ethane has an absorption band in the same 2.3 µm region as methane. FIG. 21 shows a transmission spectrum of a 100 ppm-m sample of ethane and, for reference, methane. These spectrums were calculated from the PNNL database and show the spectra at 1 atm pressure. The data seems to show that the ethane spectra is very dense, approaching a continuum absorption. It also seems to show that the absorption by ethane is weaker than methane. However, it should be noted that the resolution of these spectra is insufficient to separate close spaced lines. As such the actual ethane spectra may be more structured than this data shows. This dataset provides moderate resolution spectral absorption features of various gases and vapours at low concentration mixed in 1 atm of air or $N_2$. The ethane band mostly overlaps the methane band, so an instrument designed for methane may be used to test ethane sensitivity.

Energy Models

The 2.3 µm system was modeled to determine the amount of energy which can be gathered. The sensitivity of the system will depend on the noise-to-signal ratio (NSR) it can achieve. Smaller NSR means higher potential sensitivities of the instrument.

An energy model analysis is show for four different 2.3 µm $CH_4$ sensing systems, with the results listed in Table 2. The first two systems listed assume an off-the-shelf InGaAs camera system by Xenics (Xeva-2.5-320), with the wide and narrow bandpasses (Wide: 4150 to 4450 $cm^1$, 300 $cm^{-1}$ wide; Narrow: 4175 to 4275 $cm^1$, 100 $cm^{-1}$ wide). The next two systems assume a system identical to the current realSens™, but with InGaAs detectors tuned to 2.3 µm, again with the wide and narrow bandpasses. For reference the fifth system in the energy model is the 3.3 µm realSens™

TABLE 2

Energy model for three models of realSens type instruments

| | 2.3 µm realSens | 3.3 µm realSens | | |
|---|---|---|---|---|
| Detector: | Xenic Xeva-2.5-320 (InGaAs) | Custom InGaAs (realSens-like) | InSb | |
| Bandpass | Wide | Narrow | Wide | Narrow |
| Altitude | 300 m | | | |
| Swath | 64 m | | | |
| Focal Length | 45 mm | 150 mm | | |
| FPA | 320 × 256 InGaAs | 32 × 1 InGaAs | 32 × 1 InSb | |
| Pixel Pitch | 30 µm | 1000 × 1400 µm | | |
| FPA Dimension | 9.6 × 7.68 mm | 32 × 1.4 mm | | |
| Pixel FOV | 0.2 × 0.2 m | 2.0 × 2.8 m | | |
| Binned-Pixel | 10 × 14 pixels | | | |
| b-Pixel Area | 300 × 420 µm | | | |
| b-Pixel FOV | 2.0 × 2.8 m | | | |
| (b-)Pixel Area | 0.126 $mm^2$ | 1.4 $mm^2$ | | |
| Fore-Optic Diam. | 38 mm | 200 mm | | |
| F/# | F/1.18 | F/0.75 | | |
| Angle on Pixel | 22.9° | 33.7° | | |
| Fore-Optics Ω | 0.495 sr | 1.055 sr | | |
| Eff. Etendue | $2.49 \times 10^{-8}$ $m^2$ sr | $5.91 \times 10^{-7}$ $m^2$ sr | | |
| REF Radiance | 0.227 W $m^{-2}$ $sr^{-1}$ | 0.065 W $m^{-2}$ $sr^{-1}$ | 0.227 W $m^{-2}$ $sr^{-1}$ | 0.065 W $m^{-2}$ $sr^{-1}$ |
| COR Radiance | 0.156 W $m^{-2}$ $sr^{-1}$ | 0.041 W $m^{-2}$ $sr^{-1}$ | 0.156 W $m^{-2}$ $sr^{-1}$ | 0.041 W $m^{-2}$ $sr^{-1}$ |
| REF | $5.67 \times 10^{-9}$ W | $1.62 \times 10^{-9}$ W | $1.34 \times 10^{-7}$ W | $3.84 \times 10^{-8}$ W |
| COR | $3.89 \times 10^{-9}$ W | $1.03 \times 10^{-9}$ W | $9.22 \times 10^{-8}$ W | $2.43 \times 10^{-8}$ W |
| D* | $2 \times 10^{11}$ cm $Hz^{1/2}$ $W^{-1}$ | $2 \times 10^{11}$ cm $Hz^{1/2}$ $W^{-1}$ | $2 \times 10^{11}$ | |
| Integration Period | 0.01 sec | | | |
| Bandwidth | 15.91 Hz | | | |
| NEP | $7.08 \times 10^{-13}$ W | $2.36 \times 10^{-12}$ W | $2.36 \times 10^{-2}$ W | |
| NSR (REF) | 0.00012 | 0.00044 | 0.00002 | 0.00006 |
| NSR (COR) | 0.00018 | 0.00069 | 0.00003 | 0.00010 |
| NSR (D2A) | 0.00022 | 0.00082 | 0.00003 | 0.00011 |
| $CH_4$ Sensitivity | 64 ppm-m | 164 ppm-m | 9 ppm-m | 23 ppm-m |

The Xenics™ system assumes a Simultaneous-View Correlation Radiometry (SVCR) system in which the FOV is focussed onto two linear strips of the long axis (320 pixels) of the FPA. It is also assumed that the fore-optics diameter was 1.5" (38 mm). To achieve a 64 m wide swath, a focal length of 45 mm was required. It was also assumed that to achieve identical FOVs as realSens, pixels would be binned. To achieve a 2.0×2.8 m FOV, 10×14 pixels would be "binned". Based on calculated REF and COR signals, the energy model determines a NSR for a Xenics 2.3 μm realSens™ detector of 0.00022 and 0.00082, for the wide and narrow bandpasses. This corresponds to a sensitivity of 64 and 164 ppm-m of $CH_4$.

The next two systems modelled were the identical to realSens™ but tuned to 2.3 μm. These models determined a sensitivity of 9 and 23 ppm-m of $CH_4$. The final system calculated was the sensitivity of the current 3.3 μm realSens. The model found a sensitivity of 32 ppm-m of $CH_4$.

Because of the relatively high sensitivity of the models, none of the modelled instruments are likely to be energy limited, and thus a simple instrument made with off-the-shelf detectors and optics may be effective.

It should be noted that the model assumed the same D* for (extended) InGaAs and InSb detectors. The detectivities of these two detectors are similar at 2.3 μm. The main difference between the two detectors is that the cut-off for InGaAs is ≈2.6 μm versus 5 μm for InSb. This allows InGaAs detectors to be operated at room-temperature (or better cooled by TE-coolers) where as InSb detectors must be cooled to LN2 temperatures.

Vehicle-Based Remote Sensing System

A system may be mounted on the roof of a vehicle looking forward. The remote sensing unit and the electronics may be separated. A visible camera may provide images of the locality of leak. A GPS/INS system may provide position and direction information. The system may be mounted on a vehicle to detect gas leaks. The vehicle may be for example a small airplane, helicopter or truck. A truck may for example be driven along a pipeline or other possible source of a gas leak.

The system may be a passive or an active system. For example, a scanning mechanism or an active mechanism using a radiation source may be used. In an active system, a light source may also be added to the system to allow the instrument to operate in cloudy and nighttime conditions.

The system may provide some information about leak location relative to vehicle. The system may also operate in real-time, and may be autonomous. It may be able to look forward 50 to 200 ft (15 to 60 m) and operate at speeds up to 50 km/h. The system may also provide significant across-track measurements.

The system may also be mounted low enough on the vehicle to not cause height problems. It may also be small and light enough to be easily handled. The system may be designed to minimise sensitivity to vibrations. The system may be operable at low power. The system may have a GPS to provide location information.

Instrument Concept

The instrument may be mounted on an airborne instrument, due to a series of factors that may allow the instrument to be small, light and relatively inexpensive to build. These factors include:

(1) At 2.3 μm, the upwelling reflected solar radiance is much higher than at 3.3 μm. This is due to (a) higher surface reflectivities, as shown in FIGS. 13-14, and (b) solar radiance at 2.3 μm is about 75% higher than at 3.3 μm (Planck's Law).

(2) The spectral band at 2.3 μm is denser than at 3.3 μm (increasing the correlation depth).
(3) The terrestrial component of upwelling radiance in extremely small (also increasing the correlation depth).
(4) IR detectors at 2.3 μm have higher potential detectivities (D*) than at 3.3 μm.
(5) Optical materials tend to be much less expensive (glass instead of Si or Ge).
(6) Detectors tend to be less expensive (InGaAs instead of InSb), and potentially off-the-shelf.

The below analysis for a vehicle-based remote sensing instrument uses a 2.3 μm realSens™ of the same optical configuration as proposed for aircraft (in this document). FIG. 22 shows a schematic of the configuration of a vehicle-mounted instrument. Table 3 lists the viewing angle (φ), the on-ground binned-pixel FOV, and the swath width (Y), as a function of the forward viewing distance for an instrument height (Z) of 3 m. Assuming a 30 m (nominal) viewing distance and an instrument height of 3 m above ground, the angle of the view relative to the surface (q) will be 5.71° and the swath width (Y) will be 6.4 m. Assuming that 10×10 pixels are binned, the FOV on the ground of the binned pixel will be 0.2×2 m.

TABLE 3

Viewing angle (φ), binned-Pixel on-ground FOV and swath width (Y), as a function of the forward view distance (X) for a 3 m high vehicle mounted realSens.

| X | φ | b-Pixel FOV |
|---|---|---|
| 10 | 16.7° | 0.067 × 0.23 m |
| 20 | 8.53° | 0.13 × 0.88 m |
| 30 | 5.71° | 0.2 × 2.0 m |
| 40 | 4.29° | 0.27 × 3.6 m |
| 50 | 3.43° | 0.33 × 5.5 m |

Figure 26:
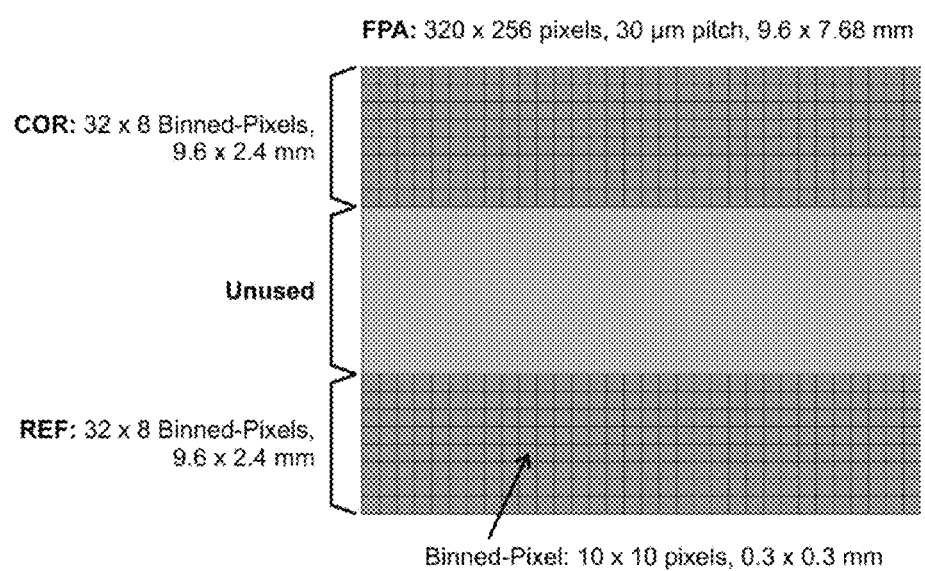
FIG. 26 is a schematic of a 320×256 pixel FPA with the proposed 32×8 binned-pixel arrays mapped.

Another option that could be implemented would be to rather than split the FPA into two linear arrays (as shown in FIG. 25); the FPA could be split into two area arrays. For example, assuming the binned pixels are 10×10 individual pixels, the FPA could be split into 8 (or more) rows. FIG. 26 shows this splitting of the FPA. This would allow a 32×8 low resolution image of the leak. If the vehicle was stopped, images or video of a leak plume could be gathered without moving. If a visible camera was part of the system, images/videos of the plume superimposed on the visible images/videos could provide further information to operators.

Regarding surface reflectivity for a passive instrument, the energy detected by a vehicle-mounted 2.3 μm realSens would be reflected solar radiance. The angle of reflection between the Sun in the sky and the viewing direction of the instrument would vary greatly, depending on the time of day, latitude, direction of travel, and slopes in the surface. Assuming that the surface is reflectively isotropic (i.e., energy is reflected equally in all directions), the energy detected by the instrument would be independent of the reflection angle. However, isotropic reflections are unlikely. It is likely that backwards scattering will be more significant than forward scattering (i.e., more signal will be detected with the Sun behind the instrument). As such the signal detected (and therefore sensitivity) will vary significantly when using a 3.3 μm instrument. However, surface emissions do not complicate retrieval with a 2.3 μm instrument, because the thermal emission from the surface is tiny or negligible.

A 2.3 μm instrument may be thermoelectrically cooled (TE-cooled) as opposed to cooled by liquid nitrogen or sterling cycle cooler. Real-time measurements may be possible since the detected radiance will be only reflected solar, reducing the complexity of data analysis.

A person skilled in the art could make immaterial modifications to the invention described in this patent document without departing from what is claimed.

The embodiments of the invention in which an exclusive property or privilege is claimed are defined as follows:

1. A method of detecting a leak of a hydrocarbon, the method comprising the steps of:
   traversing a target area with a gas filter correlation radiometer having a field of view oriented towards the target area, the gas filter correlation radiometer comprising a bandpass filter and a gas correlation cell, the bandpass filter having a bandpass including at least part of the range of 4150 cm-1 to 4450 cm-1, at least part of the range 4175 cm-1 to 4275 cm-1, and a methane peak at 4350 cm-1, and being arranged to filter radiation passing through the gas correlation cell in a first path and through an evacuated cell in a second path, the gas correlation cell containing a gas having a spectral band within the bandpass of the bandpass filter overlapping a spectral band of the hydrocarbon;
   detecting radiation that has passed through the gas correlation cell to generate a first signal;
   detecting radiation that has passed through the evacuated cell to generate a second signal; and
   comparing the first signal and the second signal to determine if the hydrocarbon is present in the target area.

2. The method of claim 1 in which the bandpass is included in the range of 4150 cm-1 to 4450 cm-1.

3. The method of claim 1 in which the gas correlation radiometer further comprises an InGaAs infrared detector.

4. A gas filter correlation radiometer configured to detect a leak of a hydrocarbon, comprising:
   a bandpass filter, a beam splitter following the bandpass filter providing a first path through the gas filter correlation radiometer and a second path through the gas filter correlation radiometer;
   a gas correlation cell on the first path, the bandpass filter having a bandpass including at least part of the range of 4150 cm-1 to 4450 cm-1, at least part of the range 4175 cm-1 to 4275 cm-1, and a methane peak at 4350 cm-1, and being arranged to filter radiation passing through the gas correlation cell, the gas correlation cell containing a gas having a spectral band within the bandpass of the bandpass filter overlapping a spectral band of the hydrocarbon;
   an evacuated cell on the second path;
   a first detector arranged to receive radiation that has passed along the first path and produce output comprising a first signal;
   a second detector arranged to receive radiation that has passed along the second path and produce a second signal; and
   detector electronics having the first signal and the second signal as input, the detector electronics being configured to compare the first signal and the second signal.

5. The gas filter correlation radiometer of claim 4 in which the bandpass is included in the range of 4150 cm-1 to 4450 cm-1.

6. The gas filter correlation radiometer of claim 4 in which the gas filter correlation radiometer further comprises an InGaAs infrared detector.

* * * * *